US00PP31692P3

(12) United States Plant Patent
Kleynhans

(10) Patent No.: US PP31,692 P3
(45) Date of Patent: Apr. 21, 2020

(54) ***LACHENALIA* JACQ. F. EX MURRAY PLANT NAMED 'RAINBOW BELLS'**

(50) Latin Name: ***Lachenalia* Jacq. f. ex Murray**
Varietal Denomination: Rainbow Bells

(71) Applicant: AGRICULTURAL RESEARCH COUNCIL, Pretoria (ZA)

(72) Inventor: Riana Kleynhans, Benoni (ZA)

(73) Assignee: Agricultural Research Council, Pretoria (ZA)

( * ) Notice: Subject to any disclaimer, the term of this patent is extended or adjusted under 35 U.S.C. 154(b) by 0 days.

(21) Appl. No.: 14/756,821

(22) Filed: Oct. 19, 2015

(65) Prior Publication Data

US 2017/0112040 P1 Apr. 20, 2017

(51) Int. Cl.
*A01H 5/02* (2018.01)
*A01H 6/12* (2018.01)

(52) U.S. Cl.
USPC ..... Plt./263.1
CPC ..... *A01H 6/12* (2018.05)

(58) Field of Classification Search
USPC ..... Plt./263.1
See application file for complete search history.

(56) References Cited

PUBLICATIONS

UPOV hit on *Lachenalia* plant named 'Rainbow Bells', ZA PBR ZA20104396, 2010.*
ARC*LNR *Lachenalia* and other Flower bulb cultivars at the ARC, R. Kleynhans and S. Venter, Jul. 2012, pp. 1-23.*
UPOV Guidelines for the Conduct of Tests for Distinctness, Homogeneity and Stability, TG/126/4 published Oct. 12, 1990, downloaded from www.upov.int/edocs/tgdocs/en/tg126.pdf on Jan. 22, 2018 (Year: 1990).*
CPVO Variety Data Sheet for Application No. 20141911, Applicant: Agricultural Research Council, Application/Filing Date Jul. 29, 2014 published Oct. 15, 2014, 1 page, Community Plant Variety Office, France.
Certificate of Grant of Plant Breeder's Right, Registration No. ZA20104393, Applicant: ARC (Agricultural Research Council), dated Apr. 20, 2010, 1 page, Department of Agriculture Forestry and Fisheries, Republic of South Africa.
CPVO Variety Data Sheet for Application No. 20141910, Applicant: Agricultural Research Council, Application/Filing Date Jul. 29, 2014, published Dec. 15, 2014, 1 page, Community Plant Variety Office, France.
Certificate of Grant of Plant Breeder's Right, Registration No. ZA20104392, Applicant: ARC (Agricultural Research Council), dated Apr. 20, 2010, 1 page, Department of Agriculture Forestry and Fisheries, Republic of South Africa.
CPVO Variety Data Sheet for Application No. 20141912, Applicant: Agricultural Research Council, Application/Filing Date Jul. 29, 2014, published Oct. 15, 2014, 1 page, Community Plant Variety Office, France.
Certificate of Grant of Plant Breeder's Right, Registration No. ZA20104394, Applicant: ARC (Agricultural Research Council), dated Apr. 20, 2010, 1 page, Department of Agriculture Forestry and Fisheries, Republic of South Africa.
CPVO Variety Data Sheet for Application No. 20141915, Applicant: Agricultural Research Council, Application/Filing Date Jul. 29, 2014, published Dec. 15, 2014, 1 page, Community Plant Variety Office, France.
Certificate of Grant of Plant Breeder's Right, Registration No. ZA20104396, Applicant: ARC (Agricultural Research Council), dated Apr. 20, 2010, 1 page, Department of Agriculture Forestry and Fisheries, Republic of South Africa.
CPVO Variety Data Sheet for Application No. 20141914, Applicant: Agricultural Research Council, Application/Filing Date Jul. 29, 2014, published Dec. 15, 2014, 1 page, Community Plant Variety Office, France.
Certificate of Grant of Plant Breeder's Right, Registration No. ZA20104397, Applicant: ARC (Agricultural Research Council), dated Apr. 20, 2010, 1 page, Department of Agriculture Forestry and Fisheries, Republic of South Africa.
CPVO Variety Data Sheet for Application No. 20141913, Applicant: Agricultural Research Council, Application/Filing Date Jul. 29, 2014, published Dec. 15, 2014, 1 page, Community Plant Variety Office, France.
Certificate of Grant of Plant Breeder's Right, Registration No. ZA20104395, Applicant: ARC (Agricultural Research Council), dated Apr. 20, 2010, 1 page, Department of Agriculture Forestry and Fisheries, Republic of South Africa.
Co-Pending U.S. Appl. No. 14/756,801, inventor Kleynhans, R., filed Oct. 15, 2015 (Not Published).
Co-Pending U.S. Appl. No. No. 14/756,803, inventor Kleynhans, R., filed Oct. 15, 2015 (Not Published).
Co-Pending U.S. Appl. No. 14/756,802, inventor Kleynhans, R., filed Oct. 15, 2015 (Not Published).
Co-Pending U.S. Appl. No. 14/756,819, inventor Kleynhans, R., filed Oct. 19, 2015 (Not Published).
Co-Pending U.S. Appl. No. 14/756,820, inventor Kleynhans, R., filed Oct. 19, 2015 (Not Published).
Niederwieser, J.G., and Vcelar, B., "Regeneration of *Lachenalia* Species from Leaf Explants," *HortScience* 25(6):684-687, American Society for Horticultural Science, United States (1990).
Slabbert, M.M., and Niederwieser, J.G., "In vitro bulblet production of *Lachenalia," Plant cell Reports* 18:620-624, Springer-Verlag, Germany (1999).

* cited by examiner

*Primary Examiner* — Anne Marie Grunberg
(74) *Attorney, Agent, or Firm* — Sterne, Kessler, Goldstein & Fox P.L.L.C.

(57) ABSTRACT

A new and distinct form of *Lachenalia* plant characterized by a bulb plant type having a spreading growth habit of a height of 15-30 centimetres (cm) and width of 10-15 cm; a bell-shaped multicolored yellow, orange and red flower.

2 Drawing Sheets

*LACHENALIA* JACQ. F. EX MURRAY PLANT NAMED 'RAINBOW BELLS'

Genus and species: *Lachenalia* Jacq. f. ex Murray.
Variety denomination: 'Rainbow Bells'.

BACKGROUND OF THE INVENTION

The present invention relates to a new and distinct cultivar of *Lachenalia*, botanically known as *Lachenalia* Jacq. f. ex Murray having the common name of Viooltjies/Cape cowslip and hereinafter referred to by its variety denomination 'Rainbow Bells'.

The variety was first cultivated in 2008 and originated by means of conventional breeding by the inventor during 2009 to 2010 at the premises of Agricultural Research Council Vegetable and Ornamental Plant Institute, Roodeplaat, Pretoria, Republic of South Africa.

Asexual reproduction of the 'Rainbow Bells' plant at the same location has shown that the unique features thereof are stable and reproduced true to type in successive generations of asexual reproduction.

SUMMARY OF THE INVENTION

The present invention constitutes a new and distinct variety of *Lachenalia* which originated from an inter-species cross between two different accessions of *Lachenalia flava* as detailed herein below.

The following traits have been repeatedly observed and are determined to be the unique characteristics, under the local evaluation conditions, of the 'Rainbow Bells' plant. These characteristics in combination distinguish 'Rainbow Bells' as a new and distinct *Lachenalia* cultivar:

1. Bulb plant type having a spreading growth habit of a height of 15-30 centimeters (cm) and width of 10-15 cm.
2. Flower color: red (RHS #53A) when opening, yellow (RHS #9A) when open; multicolored yellow (RHS #9A), orange (RHS #32A) and red/maroon (RHS #45A) tip.
3. Flower form: Bell shaped.

Color references are made to The R.H.S. Color Chart, 1$^{st}$ edition, 1966, except where general color terms of ordinary significance are used or indicated otherwise.

Plants of the new *Lachenalia* variety 'Rainbow Bells' can be compared to similar denominations such as 'Romelia' and 'Namakwa'. 'Romelia' has plain yellow bell-shaped flowers whereas 'Rainbow Bells' has multicolored bell-shaped flowers having an orange (RHS #32A) base, turning yellow (RHS #9A) ending in a red/maroon (RHS #45A) tip. 'Romelia' does not have widely recurving tips like 'Rainbow Bells', but the stamens are included as opposed to the exerted stamens of 'Rainbow Bells'. The inflorescence is not as dense as that of 'Rainbow Bells'. The flowers of 'Rainbow Bells' are furthermore shorter than those of 'Romelia'. 'Namakwa' has plain yellow flowers with reddish tips and are of tubular shape. The flower orientation of 'Namakwa' is horizontal whilst the orientation of 'Rainbow Bells' is hanging.

BRIEF DESCRIPTION OF THE DRAWINGS

The first drawing illustrates the overall appearance of the 'Rainbow Bells', showing the colors as true as it is reasonably possible to obtain in colored reproductions of this type. The first drawing comprises a front perspective view of a typical 'Rainbow Bells' grown in an indoor nursery.

The second drawing illustrates the overall appearance of the 'Rainbow Bells', showing the colors as true as it is reasonably possible to obtain in colored reproductions of this type. The second drawing comprises a front perspective view of a typical 'Rainbow Bells' grown in an indoor nursery.

DETAILED DESCRIPTION

The aforementioned drawings, following observations and measurements describe 'Rainbow Bells' grown by the inventor on behalf of Agricultural Research Council Vegetable and Ornamental Plant Institute, Roodeplaat, Pretoria, Republic of South Africa. Thereafter 'Rainbow Bells' was made subject of a South African Plant Breeders' Right application in March 2009. This application was granted in 2010 under number ZA20104396.

The plant may be used for landscaping and should be planted during the month of March; indoors and in pots only. The plant should be kept at temperatures of 20-25 degrees Celsius during the day and 10-15 degrees Celsius at night. Plenty of light should be provided.

'Rainbow Bells' is an early flowering cultivar with an exceptional keeping quality.

'Rainbow Bells' originated from an inter-species cross between *Lachenalia flava* accession number L102 (female parent) and *Lachenalia flava* accession number L144 (male parent).

The female parent has pure yellow flowers with spots on the leaves, whereas the male parent has plain yellow flowers with widely recurving tips and spots on the leaves.

A specific seedling with number 1996/32/21 was selected from the parental cross described above and thereafter asexually propagated. The asexual progeny of this seedling is the cultivar 'Rainbow Bells' and was multiplied via tissue culture at the premises of Agricultural Research Council Vegetable and Ornamental Plant Institute, Roodeplaat, Pretoria, Republic of South Africa.

The following characteristics of 'Rainbow Bells' are described with reference to description of said characteristic which are comparable with the mentioned variety/ies having said similar characteristic.

Leaf:

| Characteristic: | Description of 'Rainbow Bells': | Variety having similar characteristics: |
|---|---|---|
| Attitude: | Semi-erect | 'Romaud' |
| Length: | Medium - 20 cm | 'Bontrok', 'Winsome' |
| Width: | Medium - 3.7 cm | 'Rosabeth' |
| Ratio length/width: | Large (elongated): 5.4:1 | 'Rodelein' |
| Shape: | Oblong | 'Romargo' |
| Color: | Light green (RHS #143B) | 'Romelia' |
| Leaf color designation for lower sides of the leaf | Light green (RHS #143B) | |
| Shape in cross section: | Angular | 'Robyn', 'Romelia' |
| Recurving of margin: | Absent | 'Eliza', 'Rodelein' |
| Undulation of margin: | Absent | 'Romelia' |
| Blistering of upper side: | Absent | 'Rodelein', 'Rosabeth' |
| Pubescence of upper side: | Absent | 'Rodelein', 'Rosabeth' |
| Number of spots per leaf | Not applicable | |
| Spots on upper side: | Absent | 'Rodelein' |
| Markings on outer side of leaf base: | Absent | 'Rodelein' |

Peduncle:

| Characteristic: | Description of 'Rainbow Bells': | Variety having similar characteristics: |
|---|---|---|
| Length: | Medium - 13 cm | 'Rosabeth' |
| Peduncle color designation | Light green (RHS #141C) | |
| Spots or markings: | Absent | 'Rodelein', 'Sonni' |
| Coloration of peduncle spots | Not applicable | |
| Density of peduncle spots | Not applicable | |

Bud:

| Characteristic: | Description of 'Rainbow Bells': |
|---|---|
| Color | Orange-red (RHS #-34A of RHS color chart, 2nd edition, 1986) |

Inflorescence:

| Characteristic: | Description of 'Rainbow Bells': | Variety having similar characteristics: |
|---|---|---|
| Length: | Short to medium - 8.5 cm | |
| Rudimentary apex: | Inconspicuous | 'Rosabeth' |
| Number of flowers: | Few to medium (15-25 flowers) | |

Flower:

| Characteristic: | Description of 'Rainbow Bells': | Variety having similar characteristics: |
|---|---|---|
| Description of floral organs | Inflorescence containing individual bell-shaped, pendulous flowers attached with pedicels to the peduncle | |
| Attitude: | Pendulous | 'Romelia' |
| Pedicel: | Present | 'Romelia' |
| Length of pedicel: | Medium (2-3 millimeter (mm)) | 'Bontrok', 'Louis' |
| Flower length: | Medium - 2.6 cm | 'Lizelle', 'Rolene' 'Sonni' |
| Diameter excluding apex: | Medium to large - 1.1 cm | |
| Diameter at apex: | Medium to large - 1.6 cm | |
| Attitude of distal part of inner perianth segments: | Spreading | 'Rozanne' |
| Glossiness: | Present | |
| Predominant color: | Yellow (RHS #9A) | 'Romelia' |
| Intensity of predominant color: | Strong | 'Romelia', 'Winseme' |
| Outer perianth segment: color of basal part just before opening of flower | Orange-red (RHS #-34A of RHS color chart, 2nd edition, 1986) | |
| Outer perianth segment: color of basal part of fully opened flower | Yellow-orange (RHS #-17B of RHS color chart, 2nd edition, 1986) | |
| Outer perianth segment: color of apex relative to other part | Clearly different | 'Ronette' |
| Outer perianth segment: color of apex if clearly different from other part | Yellow-green (RHS #150A) | 'Bontrok', 'Leipoldt', 'Roinge' |
| Inner perianth segment: distinct spot in middle of apex | Absent | 'Bontrok' |
| Inner perianth segment: color of margin of apex relative to other part | Clearly different | 'Louis', 'Roinge' |
| Inner perianth segment: color of differently colored margin of apex | Brown (RHS #162C) | 'Roinge', 'Bontrok' |
| Inner perianth segment: predominant color of exposed part (excluding differently colored margin of apex) | Yellow-orange (RHS #-17C of RHS color chart, 2nd edition, 1986) | |
| Length of inner perianth segment compared to outer segments: | Much longer | 'Romelia' |
| Extrusion of stamens: | Present | 'Louis', 'Rolene' |
| Fragrance: | Absent | 'Romelia' |
| Bulb: predominant shape | Oblate | 'Romaud' |
| Time of flowering: | Very early - flowering time vary from May to June (Southern Hemisphere) | 'Romaud', 'Romeila', 'Ronette' |
| Duration of flowering: | Medium (1-2 months) | 'Rodelein', 'Roinge' |

Others:

| Characteristic: | Description of 'Rainbow Bells': |
|---|---|
| Description of the bulb including size and color of the bulb at maturity | Cream/white (color designation - RHS #158B) Size: between 1.5 to 2 cm in diameter |
| Time of leaf growth/bud burst | Starts within the first week of watering (normally March/April in Southern Hemisphere) |
| A description of any fruit and seed set | No seed or fruit |
| Timing of leaf senescence | After flowering has completed and starts to die down, the leaves start to die off (wheat color) and plant dry out (September - October in Southern Hemisphere) |

The variety is not genetically modified and has been tested to be free of Ornithogalum Mosaic Virus.

The invention claimed is:

1. A new and distinct variety of *Lachenalia* plant named 'Rainbow Bells' as illustrated and described herein.

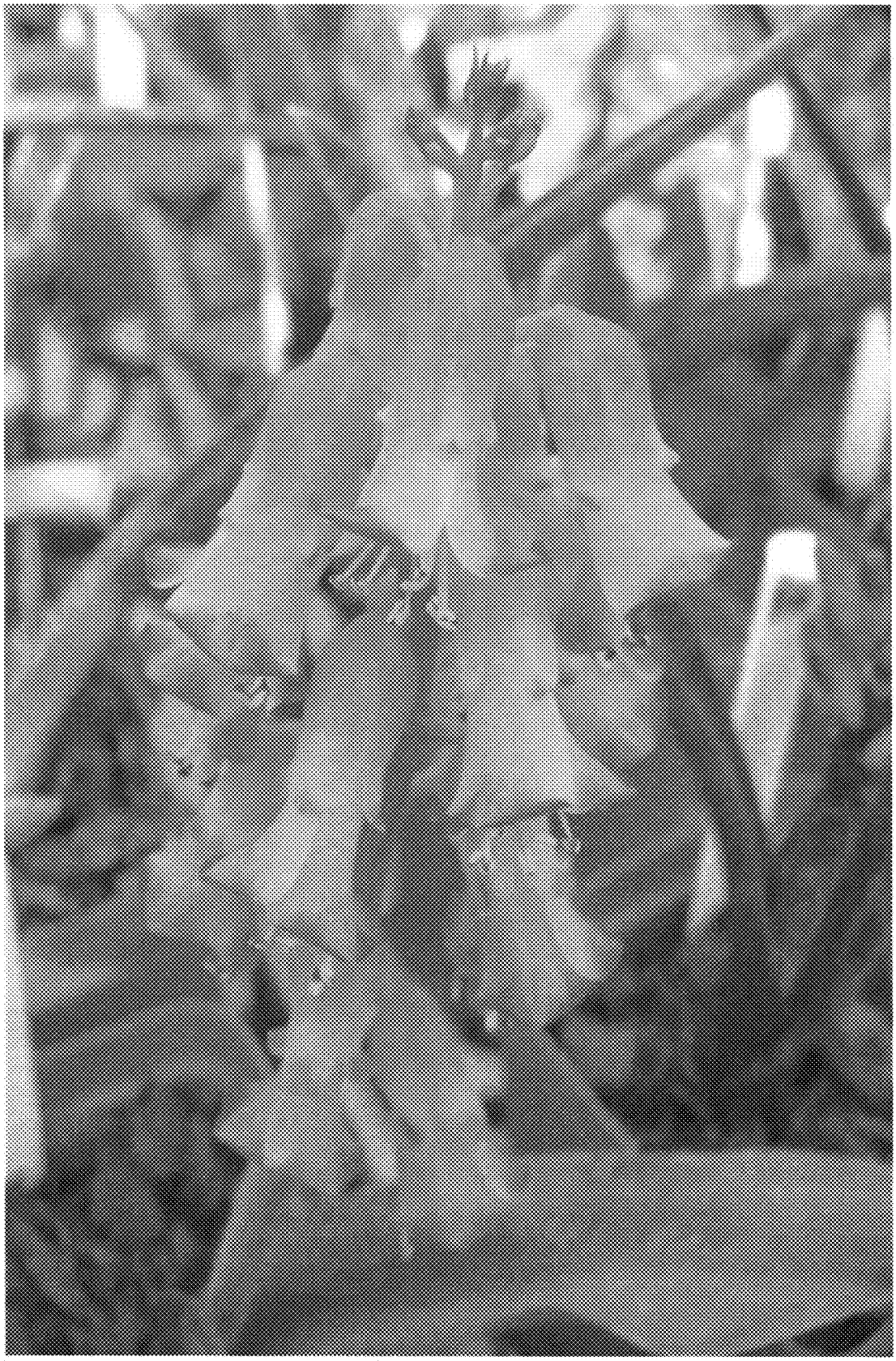

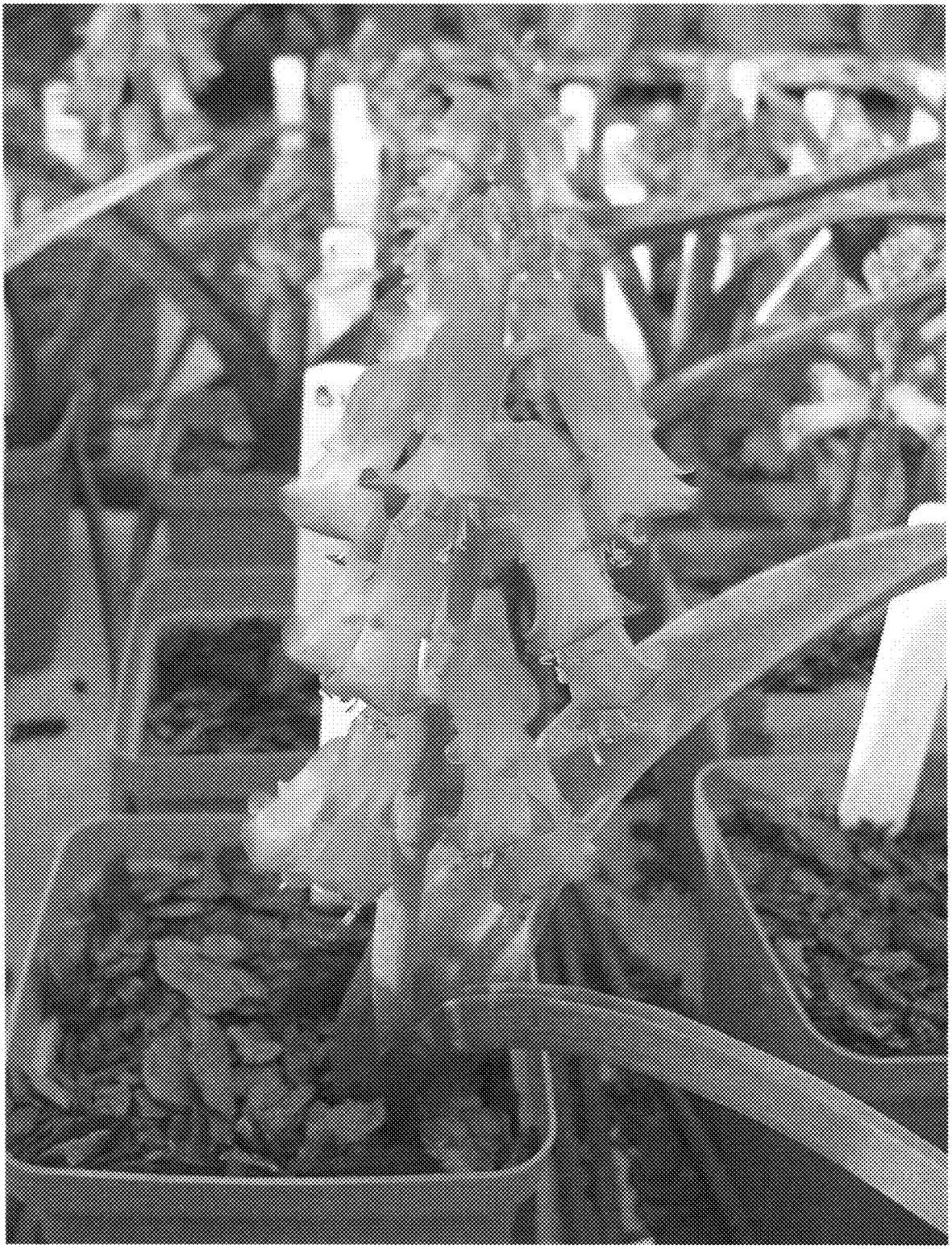

* * * * *